US008268363B2

(12) United States Patent
Flavin-Koenig

(10) Patent No.: US 8,268,363 B2
(45) Date of Patent: Sep. 18, 2012

(54) PHARMACEUTICAL COMBINATION PREPARATION CONTAINING GLYCYRRHIZINE, ZINC, AND A COMPOUND COMPRISING A THIOL GROUP OR A GROUP THAT IS METABOLIZED THERETO

(76) Inventor: Dana Flavin-Koenig, Greenwich, CT (US)

(*) Notice: Subject to any disclaimer, the term of this patent is extended or adjusted under 35 U.S.C. 154(b) by 0 days.

(21) Appl. No.: 10/570,689

(22) PCT Filed: Sep. 3, 2004

(86) PCT No.: PCT/EP2004/009814
§ 371 (c)(1),
(2), (4) Date: Mar. 6, 2006

(87) PCT Pub. No.: WO2005/023240
PCT Pub. Date: Mar. 17, 2005

(65) Prior Publication Data
US 2007/0031510 A1 Feb. 8, 2007

(30) Foreign Application Priority Data
Sep. 4, 2003 (DE) .................................. 103 40 845

(51) Int. Cl.
| | | |
|---|---|---|
| *A01N 59/16* | (2006.01) | |
| *A01N 59/20* | (2006.01) | |
| *A61K 31/315* | (2006.01) | |
| *A61K 33/32* | (2006.01) | |
| *A61K 33/04* | (2006.01) | |
| *A61K 36/48* | (2006.01) | |

(52) U.S. Cl. ........ 424/641; 424/637; 424/643; 424/703; 424/757; 514/494

(58) Field of Classification Search .................. 424/641, 424/637, 703, 757, 643; 514/494
See application file for complete search history.

(56) References Cited

U.S. PATENT DOCUMENTS
5,770,217 A * 6/1998 Kutilek et al. ................. 424/442
2002/0136782 A1 9/2002 Fleischner
2002/0142025 A1* 10/2002 Hageman ....................... 424/439

FOREIGN PATENT DOCUMENTS
| CN | 1080174 A | 1/1994 |
| GB | 841 058 | 7/1960 |
| WO | 03057233 | 7/2003 |

OTHER PUBLICATIONS

Botanical.com, web.archive.org/web/19970228070755/http://botanical.com/botanical/mgmh/l/liquor32.html, 1997, 1-10.*
Subhuti Dharmananda: "Chinese Herbal Medicine for the Treatment of Hepatitis B Infection" Internet Article, Online! 1997, XP002332842.

Database WPI Section Ch, Week 199712 Derwent Publications Ltd. London, GB; AN 1997-119476 XP002332725.
Flavin-Koenig D F: "The reversal of Epstein Barr virus iduced hepatosplenomegaly in 24 hours with inhibitors of xanthine oxidase and nitric oxide synthase" The New Zealand Medical Journal Mar. 22, 1996, vol. 109, No. 1018, pp. 106-107. p. 107 is not available at this time.
Meletis CD "Cough control the natural way" Alternative and Complimentary Therapies 2000 United States Bd. 6, Nr. 1, 2000, XP 009049488.
Coon J T: "Evidence for complementary therapies for the treatment of hepatitis C infection" Focus on Alternative and Complimentary Therapies, Mar. 2004 United Kingdom Bd. vol. 9, Nr. 1, 2004, Seiten 7-11, XP 009049489.
International Search Report PCT/EP2004/009814 mailed Aug. 22, 2005.
English Translation of Written Opinion of the International Searching Authority PCT/EP2004/009814 dated Aug. 18, 2005.
International Preliminary Report on Patentability PCT/EP2004/009814 dated Jul. 3, 2006.
Database WPI Section Ch, Week 199712 Derwent Publications Ltd. London, GB; AN-1997-128646 XP-002196610; AN-1997-276683 XP-002196618; AN-1996-205436 XP-002182609.
Dana F. Flavin "Reversing Splenomegalies in Epstein Barr Virus Infected Children: Mechanisms of Toxicity in Viral Diseases" Journal of Orthomolecular Medicine vol. 21, No. 2, 2006 pp. 95-101.
Charles Daniel, former About.com Guide, "The Big List of Acute Viral Hepatitis Symptoms", About.com article, updated Mar. 23, 2012, pp. 1-4.
"Hepatitis A, Acute", Harrison's Practice Answers on Demand, McGraw Hill, updated Jan. 14, 2009, pp. 1-11.
"Hepatitis B, Acute", Harrison's Practice Answers on Demand, McGraw Hill, updated Jul. 16, 2009, pp. 1-2.
Charles Daniel, former About.com Guide, "Hepatitis B Virus Infection", About.com article, updated Jul. 16, 2009, pp. 1-4.
Robert S. O'Shea, "Hepatitis B", Cleveland Clinic, Center for Continuing Education, Jan. 1, 2009, pp. 1-18. Copyright (c) 2000-2011.
Johns Hopkins Medicine Gastroenterology & Hepatology, "Viral Hepatitis B: Introduction", Downloaded from http://www.hopkins-gi.org/GDL_Disease.aspx?CurrentUDV=31&GDL_Disease_ID=554180E5-387E-4246-9AB9-D29E025D417F&GDL_DC_ID=9AA60584-3607-4D15-A459-BD3F67A3A4A7, pp. 1-4; pp. 1A-4A; pp. 1B-3B, 2012.
Robert S. O'Shea, "Hepatitis B", Cleveland Clinic, Center for Continuing Education, Jan. 1, 2009, pp. 1-11. Copyright (c) 2000-2011.
Charles Daniel, "Hepatitis B Virus Infection", former About.com Guide, updated Jul. 16, 2009, pp. 1-2.
"Hepatitis A, Acute", Harrison's Practice Answers on Demand, McGraw Hill, updated Jan. 14, 2009, p. 1.
Joanna Thompson Coon, "Evidence for complementary therapies for the treatment of hepatitis C infection", Pharmaceutical Press, 2005.

(Continued)

*Primary Examiner* — Abigail Fisher
(74) *Attorney, Agent, or Firm* — Roberts Mlotkowski Safran & Cole P.C.

(57) ABSTRACT

The invention relates to the application of a combination including all forms of zinc or zinc substances, at least one of an orally applied combination of a free thiol group or a group that is metabolized to a free thiol in a mammal, and as the only pure plant part, glycyrrhicinic acid or the substance from succus liquiritiae, for the production of a medication to fight acute or chronic viral infections. The free thiol group or the group that is metabolized to a free thiol in a mammal is derived from N-acetylcysteine, methionine, cysteine, allylcysteine, alpha lipoic acid, or sulfur.

18 Claims, No Drawings

OTHER PUBLICATIONS

Subhuti Dharmananda, "Chinese Herbal Medicine for the treatment of hepatitis B infection", Institute for Tradional Medicine, May 1997, Portland, Oregon.

Dana F. Flavin-Koenig "The reversal of Epstein Barr virus induced hepatosplenomegaly in 24 hours with inhibitors of xanthine oxidase and nitric oxide synthase" Letters, New Zealand Medical Journal, Mar. 22, 1996.

The Merck Index Fourteenth Edition pp. 777-778, 2006.

Dana F. Flavin "Reversing Splenomegalies in Epstein Barr Virus Infected Children: Mechanisms of Toxicity in Viral Deseases" Journal of Orthomolecular Medicine vol. 21, No. 2, 2006.

NCBI Pubchem Substance Same Substances for Pubchem Substance (Select 7847225) Pubchem Substance Results pp. 1 and 3, 2010.

* cited by examiner

PHARMACEUTICAL COMBINATION PREPARATION CONTAINING GLYCYRRHIZINE, ZINC, AND A COMPOUND COMPRISING A THIOL GROUP OR A GROUP THAT IS METABOLIZED THERETO

The invention consists of a pharmaceutical or nutrient combination preparation, of glycyrrhicinic acid, zinc and an orally acceptable connection to a free thiol group or a group that can be metabolized to a thiol group in a mammal's body. The invention further relates to a use for application for fighting viral infections especially Flu types of viruses.

Glycyrrhicinic acid (or glycyrrhicin) is an integral part of the root of Glycyrrhizia glabra LINNÉ (commonly called Licorice) with the following structural formula:

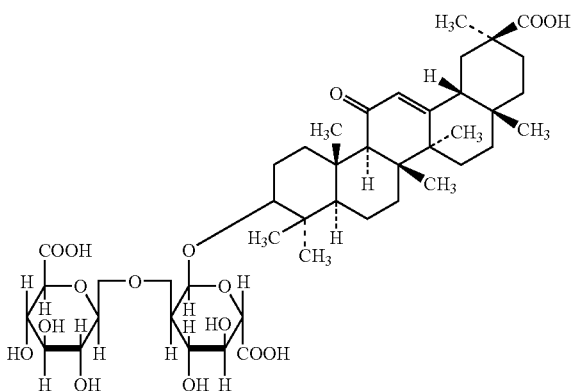

The natural, unpeeled dried root of glycyrrhiqia glabra is known as licorice root, and used as a medication in the natural healing arts. Liquid and solid forms for oral intake are known as succus liquiritiae. Licorice is made of such succus liquiritiae with a concentration of glycyrrhicinic acid of more than 1%. In natural medicine, licorice root is used for catarrh, in the upper airways, and ulcers in the stomach and duodenum. In catarrh the expectorant, mucolytic and anti-inflammatory actions of the medication are most known.

In animal studies, glycyrrhicinic acid has shown an interferon inducing effect, connected to an antiviral effect. It also shall have a direct antiviral effect. Zinc is also known as a trace element that is imperative for the Immune system. In cases of viral infection, when zinc is taken, it increases the interferon activity to a multiple. In addition, zinc has a direct antiviral activity on the viral replication.

Thiol containing substances have many therapeutic acitivities. In connection to this invention, it is especially meaningful that thiol groups increase the number of antiviral functioning lymphocytes, e.g. the Th-1 lymphocytes and natural killer cells which are the sources for interferon especially interferon alpha and interferon gamma. The increase in the number of functioning competent immune cells is the result of the binding of the thiol group to nitric oxide. The concentration of nitric oxide (NO) is elevated in viral infections and responsible for the immobilization of the antiviral lymphocytes, which weakens the natural endogenous defense against viral infections.

In Japan there is a combination preparation of glycyrrhicinic acid, glycine and cysteine on the market to treat chronic viral hepatitis and post hepatic liver cirrhosis. The purpose of the invention is to create a synergistic antiviral activity that is greater than one would expect from an application of the individual components.

This purpose is met through the composition according to claim 1 and the usage according to claim 8.

The inventor surprisingly discovered the combination of glycyrrhicinic acid, zinc and a thiol containing group, or metabolized to a thiol containing group had an astounding antiviral activity.

The combination of substances can be in the form of three separate preparations (or "application units"), in a single package. It could also be any two of the substances worked into one combined substance (or "one combined preparation"). Further all three substances could be formed together into one combination substance (or "one combined preparation").

Glycyrrhicinic acid is preferentially applied in the invention in the form of succus liquiritiae. Succus liquiritiae can be a liquid or a dried powder, which as mentioned above is obtained from the licorice root. A preferable succus liquiritiae liquid contains 5% glycyrrhicinic acid (50 mg/ml)

The oral dose of glycyrrhicinic acid is preferably 750 mg to 2000 mg, such as 1500 mg to 2000 mg per day for adults. It is preferred to be given in two or three doses per day, especially preferred in three doses.

Zinc can be used in all typical pharmaceutical acceptable forms, including zinc orotate, zinc aspartate, zinc histidine, zinc sulfate, for the combination preparation according to the invention. The preferred oral dose for adults is 50 mg to 150 mg, such as 75 mg to 150 mg per day (referring to the element zinc). The daily dosage of zinc is also preferred to be portioned, e.g. three times a day.

The oral application of a free thiol group or a group that is metabolized to a free thiol group in mammals is chosen preferably from N-acetylcysteine, Methionine, Cysteine, allylcysteine, alpha lipoic acid and Sulfur. Especially preferred is N-acetylcysteine, as this has also a mucolytic activity. All available preparations presently on the market are suitable including but not exclusively, ACC® from Hexal, Fluimucil® from Zambon etc.

This group of thiol containing substances is preferred at the doses of 600 mg to 2400 mg, such as 1200 mg to 2400 mg for adults preferentially applied in divided doses per day, e.g., three divided doses.

The daily doses of the individual substances for children is preferentially half of the adult doses.

The inventions combination preparation may contain additional pharmaceutical substances eg. paracetamol or acetyl salicylic acid.

The active substances of the inventions combination preparation is preferentially for oral application, although a parenteral, topical, intranasal, intravaginal and rectal application is not ruled out. Oral application forms include tablet, capsule, pill, buccal tablet, elixir, suspensions, syrups and similar forms. These application forms can include appropriate carriers eg dicalsium phosphate, binders such as gums, including gum arabicum, corn starch, or gelatine, breakdown products such as corn starch, potato starch, and Alginin acid, lubricants, such as magnesium stearate, sweetening substances, taste enhancers and all other commonly used enhancing and support subtances used in the pharmaceutical industry.

The invention combination preparation is for fighting acute and chronic, preferentially acute, virus infections for example, but not limited to corona viruses, rhino viruses, coxsackie viruses, Influenza A- and B-viruses, Herpses viruses, cytomegaloviruses, hepatitis A-, B- and C-viruses, Epstein-Barr-virus, and other viruses causing colds and all flu infections. This is especially applicable to infections of the upper respiratory tract.

It was surprisingly found that the combination preparation of the above three substances had an astounding synergistic activity.

In clinical studies each single substance was tested in flu symptoms (colds, flu, viral infection of the upper respiratory tract) whose duration without treatment normal lasted 7 days.

The results obtained were:
a) Zinc as a single treatment:
125mg per day, divided in three doses:
Slight lessening of the duration of the illness to an average of 5 days.
On a scale of 1-10 (1 least effect, 10 maximum effect):2
b) N-Acetylcysteine
2400 mg, divided in three doses;
Moderate reduction of duration of illness to an average of 4 days.
On a scale of 1-10 (1 least effect, 10 maximum effect):5
c) Glycyrrhicinic acid
1500 mg, divided in three doses;
Slight reduction in the duration of illness to an average of 5.0 days;
On a scale of 1-10 (1 least effect, 10 maximum effect):2

The average duration of illness with the treatment combination of all three of the above substances a), b), and c) in the majority of the cases the duration of the illness was shortened to 24 hours or less. Exactly said: 30 adults (men and women) had an improvement in symptoms (decreasing tiredness and malaise) already after 30 to 60 minutes after taking the first dose of the combination of a), b), and c). 24 hours later, 85% of the patients were completely without symptoms and able to return to work. The maximum duration in a few cases lasted 5 days.

90% of the patients stayed healthy. 10% of the patients who did not follow the suggestions to avoid alcohol and to have a full nights sleep, showed new symptoms which however after taking the treatment again quickly subsided.

Further, 20 children between the ages of 7 to 15 years old were treated with half of the doses from the combination of a) b) and c). The results were the same as for the adults. That is, after 30 to 60 minutes a significant improvement of the symptoms was seen and after 24 hours, most of the children were completely without signs of illness so that they could return to school the next day.

This surprising synergy of the combination of the above three substances a), b) and c) was not to be expected. It was known for some time that glycyrrhicinic acid had antiviral activity, but the incredible enhancement of activity with zinc and thiols that lead to an extraordinary increase in the elimination of symptoms was not discovered before the development of the combination therapy.

The preparation in the invention is not only useful for those ill, but of great use also for the economy in that the symptoms of diseases causing inability to work (colds, flu's) can be eliminated in a short period of time. Side effects in the short duration of therapy are not observed.

The following examples elucidate the invention further:

EXAMPLES

In all examples the application of the combined individual doses was 500 mg glycyrrhinic acid (or about 10 ml (a small tablespoon) succus liquiritiae depuratus solutus 1+1 from the company Dr. Hetterich GmbH & Co. KG, Fuerth, Bavaria), 50 mg Zinc (as an element in the form of zinc orotate) and 800 mg N-Acetylcysteine. Patients with high fevers (above 38.5° C.) were given paracetamol in addition to the treatment to decrease the fever. (Slight fevers did not require any special treatment)

Example 1

A 12 year old girl presented with low grade fever, lethargy, tiredness, mylagia, sore throat, and general malaise following an infection (*Streptococcus* negative.) She was treated with half of the doses of the above combination and she showed improvement within an hour. The application was repeated every 6 hours (except for the night). In 24 hours she showed a general improvement and no symptoms of any virus infection and was back in school.

Example 2

A 15 year old girl was presented with fever, runny nose, watering eyes, sore throat, (*Streptococcus* negative) and mild cough. She was treated with half of the doses of the above combination. After 30 minutes the child felt better, with less malaise and lethargy, the rest of the symptoms were milder. The treatment was repeated twice after 6 hours, respectively. In 24 hours she had no symptoms. She preferred not to attend school but to stay home and rest for one more day.

Example 3

A 16 year old boy presented with myalgia, fatigue, malaise, lethargy and tiredness and fever (low grade). He was treated half of the doses of the above combination. He showed improvement in 30 minutes with more energy and less lethargy. The treatment was repeated every 6 hours (except for the night). The entire symptoms were gone in 24 hours. The boy returned to school the next day.

Example 4

A 38 year old woman, complained of fever, malaise, runny nose, myalgia, lethargy, weakness and tiredness. She was given the above combination dosage at 10 A.M. Half an hour later she had less symptoms, her lethargy was gone, but the general malaise was still evident. She received two more treatments during the day and by the next morning she could resume her daily activities without hinderness. The symptoms were all gone.

Example 5

A 52 year old woman presented with flu-like symptoms of the upper rispiratory, fever, headache, myalgia, tiredness, malaise and lethargy. She was treated with the above dosage combination and slept most of the day. Her symptoms were almost completely reduced by the second day where to be on the safe side we resumed the treatment twice on the second day. Symptoms were completely gone after the second day.

Example 6

A 42 year old man presented with fever (low grade), malaise, myalgia, sniffles, light cough and sore throat. He complained of his flu symptoms and general weakness and tiredness. He was given the above single dose of combined substances at 2: P.M. and slept until evening when he received another single dose of combined substances. The next moring he felt better and wanted to go to work, however it was recommended he take another treatment for the morning and at noon to insure that he did not have a relapse. He returned to work the next day, feeling no more symptoms or illness of any sort.

Example 7

A 58 year old man presented with flu like symptoms including fever (low grade), malaise, tiredness, myalgia, headache and sore throat. He was given the above combination in single dose three times in the first day. After the first treatment in the morning his symptoms of tiredness and malaise were reduced in 30 minutes, he was however still weak and rested the entire day. The next day he was more than 80% better but remained home the entire mornig, returning to work in the afternoon.

Example 8

A 65 year old woman complained of upper rispiratory symptoms including runny nose, sore throat, malaise, low grade fever, and light cough. She was treated with the above combination in the morning and rapidly felt better after 1 hour. She was however still with a sore throat and myalgia. The treatment was repeated twice that day and once in the following morning. Her illness was gone after 36 hours.

The invention claimed is:

1. A method of treating symptoms of upper respiratory tract infection or infections comprising administering to a person in need thereof a synergistic combination including the following components:
   a) 50 to 150 mg of a daily dose of zinc or a zinc substance, based on elemental zinc, wherein the zinc or the zinc substance is selected from the group consisting of zinc orotate, zinc aspartate, zinc histidine, zinc sulfate or a mixture thereof;
   b) 600 mg to 2400 mg of a daily dose of at least one of N-acetylcysteine, methionine, cysteine, allylcysteine, alpha lipoic acid, or sulfur;
   c) 750 mg to 2000 mg of a daily dose of glycyrrhicinic acid.

2. A method according to claim 1, wherein each of the components is included in a separate preparation.

3. A method according to claim 1, wherein two of the three components are combined in a single preparation.

4. A method according to claim 1, wherein all three components are combined in a single preparation.

5. A method according to claim 1, wherein the glycyrrhicinic acid is in the form of succus liquiritiae.

6. A method according to claim 1, wherein the combination further includes one or more pharmaceutically acceptable non-active ingredients.

7. A method according to claim 1, wherein the symptoms are caused by corona virus, rhino virus, coxsackie virus, influenza A-virus, influenza B-virus, herpes virus, herpes viruses, cytomegalo viruses, hepatitis A-virus, hepatitis B-virus, hepatitis C-virus, Epstein-Barr virus, a cold virus, a flu virus or a combination of a cold and a flu virus.

8. A method according to claim 1, wherein the combination includes the glycyrrhicinic acid in a daily dose of 1500 mg to 2000 mg, the zinc or the zinc substance in a daily dose from 75 mg to 150 mg based on elemental zinc, and the at least one of N-acetylcysteine, methionine, cysteine, allylcysteine, alpha lipoic acid, or sulfur in a daily dose from 1200 mg to 2400 mg.

9. A method according to claim 8, wherein the daily dose of each component is divided into at least two single doses.

10. A method according to claim 5, wherein the combination further includes one or more pharmaceutically acceptable non-active ingredients.

11. A method according to claim 2, wherein the separate preparations are included in one package.

12. A method according to claim 1, wherein the combination includes:
   a) 125 mg daily dose of the zinc or the zinc substance based on elemental zinc;
   b) 2,400 mg daily dose of N-acetylcysteine;
   c) 1,500 mg daily dose of the glycyrrhicinic acid.

13. A method of treating symptoms of upper respiratory tract infection or infections comprising administering to a person in need thereof a synergistic combination, wherein the combination includes:
   a. 50 mg of a daily dose of zinc or zinc orotate, based on elemental zinc;
   b. 800 mg of a daily dose of N-acetylcysteine; and
   c. 500 mg of a daily dose of glycyrrhicinic acid.

14. A method according to claim 1, wherein the combination is administered orally, parenterally, topically, intranasally, intravaginally or rectally.

15. A method according to claim 14, wherein the combination is administered orally as a tablet, a capsule, a pill, a buccal tablet, an elixir, a suspension or a syrup.

16. A method according to claim 1, wherein the combination consists essentially of the following components:
   a) 50 to 150 mg of a daily dose of the zinc or the zinc substance, based on elemental zinc;
   b) 600 mg to 2400 mg of a daily dose of the at least one of N-acetylcysteine, methionine, cysteine, allylcysteine, alpha lipoic acid, or sulfur; and
   c) 750 mg to 2000 mg of a daily dose of the glycyrrhicinic acid.

17. A method according to claim 1, wherein b) is N-acetylcysteine.

18. A method according to claim 16, wherein b) is N-acetylcysteine.

* * * * *